(12) United States Patent
Sun et al.

(10) Patent No.: US 9,381,495 B2
(45) Date of Patent: *Jul. 5, 2016

(54) RENEWABLE ISOBUTENE AND ISOPRENE FROM A MIXTURE OF ACETIC ACID AND PROPIONIC ACID

(71) Applicants: Archer Daniels Midland Company, Decatur, IL (US); Washington State University, Pullman, WA (US)

(72) Inventors: Junming Sun, Pullman, WA (US); Changjun Liu, Pullman, WA (US); Yong Wang, Pullman, WA (US); Kevin Martin, Mt. Zion, IL (US); Padmesh Venkitasubramanian, Forsyth, IL (US)

(73) Assignees: Washington State University; Archer Daniels Midland Company

( * ) Notice: Subject to any disclaimer, the term of this patent is extended or adjusted under 35 U.S.C. 154(b) by 0 days.

This patent is subject to a terminal disclaimer.

(21) Appl. No.: 14/683,272

(22) Filed: Apr. 10, 2015

(65) Prior Publication Data

US 2015/0210608 A1 Jul. 30, 2015

Related U.S. Application Data

(63) Continuation of application No. PCT/US2013/062784, filed on Oct. 1, 2013, which is a continuation of application No. PCT/US2013/063968, filed on Oct. 9, 2013, which is a continuation of application No. PCT/US2013/067256, filed on Oct. 29, 2013.

(60) Provisional application No. 61/720,433, filed on Oct. 31, 2012, provisional application No. 61/737,312, filed on Dec. 14, 2012.

(51) Int. Cl.
  *B01J 23/06* (2006.01)
  *C07C 1/207* (2006.01)
  *C07C 5/48* (2006.01)
  *B01J 37/04* (2006.01)
  *B01J 37/08* (2006.01)
  *C07C 45/52* (2006.01)
  *C07C 51/235* (2006.01)

(52) U.S. Cl.
  CPC *B01J 23/06* (2013.01); *B01J 37/04* (2013.01); *B01J 37/08* (2013.01); *C07C 1/2072* (2013.01); *C07C 5/48* (2013.01); *C07C 45/52* (2013.01); *C07C 51/235* (2013.01); *C07C 2521/06* (2013.01); *C07C 2523/06* (2013.01)

(58) Field of Classification Search
  None
  See application file for complete search history.

(56) References Cited

U.S. PATENT DOCUMENTS

2008/0306320 A1* 12/2008 Merrill ............... C08C 4/00 585/660
2011/0112344 A1*  5/2011 Chewter ............. C01B 3/22 585/302

OTHER PUBLICATIONS

Sun et al., Direct Conversion of Bio-ethanol to Isobutene on Nanosized ZnxZryOz Mixed Oxides with Ballanced Acid-Base Sites, Journal of the American Chemical Society, 2011, vol. 133, pp. 11096-11099.*

* cited by examiner

*Primary Examiner* — In Suk Bullock
*Assistant Examiner* — Philip Louie
(74) *Attorney, Agent, or Firm* — William B. Miller

(57) ABSTRACT

A process is described for making renewable isobutene and renewable isoprene, comprising converting a mixed acid feed including acetic acid and propionic acid to a product mixture including isobutene and at least one or both of 2-methyl-1-butene and 2-methyl-2-butene in the presence of a catalyst, separating isobutene from the product mixture and dehydrogenating either or both of the 2-methyl-1-butene and 2-methyl-2-butene in the remainder to provide isoprene.

12 Claims, 1 Drawing Sheet

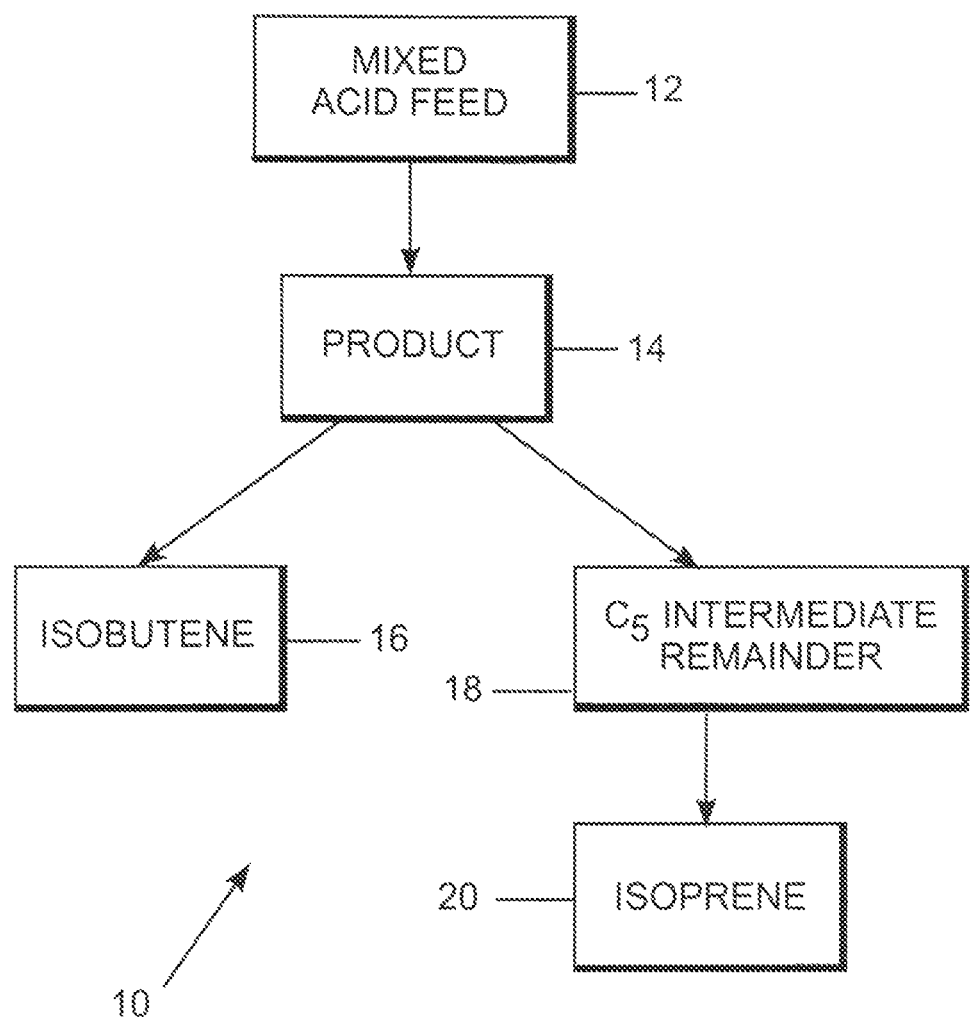

RENEWABLE ISOBUTENE AND ISOPRENE FROM A MIXTURE OF ACETIC ACID AND PROPIONIC ACID

CROSS-REFERENCE TO RELATED APPLICATIONS

The present application is a continuation of International Application No. PCT/US2013/67256, filed Oct. 29, 2013, now published as WO 2014/070733; the present application is also a continuation of International Application No. PCT/US2013/063968 filed Oct. 9, 2013, now published as WO 2014/092849, which directly claims the benefit of U.S. Provisional Application Ser. No. 61/737,312 filed Dec. 14, 2012; and, the present application is also a continuation of International Application No. PCT/US2013/062784 filed Oct. 1, 2013, now published as WO 2014/070354, which directly claims the benefit of U.S. Provisional Application Ser. No. 61/720,433 filed Oct. 31, 2012.

TECHNICAL FIELD

This application relates to methods of producing isobutene and isoprene.

BACKGROUND

As related in the '312 application, isobutene is widely used for the production of a variety of industrially important products, such as butyl rubber for example. Isobutene has been produced commercially to date through the catalytic or steam cracking of fossil feedstocks, and the development of a commercially viable process for the manufacture of isobutene from a renewable source-based feedstock has accordingly become of great interest as fossil resources are increasingly depleted and/or have become more costly to use—especially in consideration of increased demand for isobutene.

Previous to the earlier '433 application, a hard-template method had been described for synthesizing $Zn_xZr_yO_z$ mixed oxides for the direct and high yield conversion of ethanol (from the fermentation of carbohydrates from renewable source materials, including biomass) to isobutene, wherein ZnO was added to ZrO2 to selectively passivate zirconia's strong Lewis acidic sites and weaken Brönsted acidic sites while simultaneously introducing basicity. The objectives of the hard template method were to suppress ethanol dehydration and acetone polymerization, while enabling a surface basic site-catalyzed ethanol dehydrogenation to acetaldehyde, an acetaldehyde to acetone conversion via aldol-condensation/dehydrogenation, and a Brönsted and Lewis acidic/basic site-catalyzed acetone-to-isobutene reaction pathway.

High isobutene yields were in fact realized, but unfortunately, as later experienced by Mizuno et al. (Mizuno et al., "One—path and Selective Conversion of Ethanol to Propene on Scandium-modified Indium Oxide Catalysts", Chem. Lett., vol. 41, pp. 892-894 (2012)) in their efforts to produce propylene from ethanol, it was found that further improvements in the catalyst's stability were needed.

The '433 application concerned the discovery that these improvements could be realized without adding modifying metals and without a reduction in the initial high activity (100 percent ethanol conversion) that had been observed in these mixed oxide catalysts, while the '312 application concerned the further discovery that the mixed oxide catalysts we had been evaluating for converting ethanol to isobutene are also able to catalyze the conversion of acetic acid to isobutene. Since acetic acid can be made by a variety of methods from a number of different starting materials, including through carbonylation of methanol derived from sequestered carbon dioxide, for example, the capability of these mixed oxide catalysts to catalyze the conversion of acetic acid to isobutene enabled a range of options for utilizing renewable resources more efficiently, all as described in greater detail in the '312 application.

In one of these methods for making the acetic acid, namely, by fermentation from a source of five and/or six carbon sugars, propionic (or propanoic) acid is often produced in addition to acetic acid—and this is especially true where the five and/or six carbon sugars have been obtained from the hydrolysis of a lignocellulosic biomass. Most propionic acid manufactured today is used as a preservative in both animal feed as well as in food for human consumption, but extensive use of an acetic acid process according to the '312 application to meet present and foreseeable isobutene demand would certainly benefit from and perhaps require a higher value-added outlet for the propionic acid that can be co-produced with the acetic acid.

SUMMARY OF THE PRESENT INVENTION

In a first aspect, the present invention thus broadly concerns a process for making renewable isobutene and renewable isoprene from a mixture of acetic acid and propionic acid through using a mixed oxide catalyst, for example, a $Zn_xZr_yO_z$ mixed oxide catalyst, based in part on the discovery that $C_5$ intermediates are formed in addition to isobutene in a process of the type described in the incorporated '312 application using such a catalyst, which intermediates can then be converted to isoprene according to known methods.

In a second aspect, the $Zn_xZr_yO_z$ mixed oxide catalyst can be an improved stability $Zn_xZr_yO_z$ mixed oxide catalyst prepared according to the '433 application.

In another aspect, the present invention concerns an improved process for producing 1,2-propanediol (propylene glycol) by the hydrogenolysis of a feedstock selected from one or more of glycerol, the five and six carbon sugars and sugar alcohols, lactate and lactic acid in the presence of hydrogen and a suitable hydrogenolysis catalyst and under conditions which are effective for carrying out the hydrogenolysis, and wherein at least some ethylene glycol is produced, the improvement comprising dehydrating and oxidizing at least part of the ethylene glycol to form acetic acid and dehydrating and oxidizing at least part of the propylene glycol to form propionic acid, and subsequently converting at least some of the thus-formed acetic acid and at least some of the thus-formed propionic acid together to isobutene and isoprene in a process according to the first aspect described above.

Isoprene (CAS 78-79-5), like isobutene, is a commercially important material that is today produced as a byproduct in the thermal cracking of naphtha or as a side product in the production of ethylene, and that is polymerized to provide polyisoprene, a synthetic rubber, as well as being used in combination with isobutene to make butyl rubber and in the production of pressure-sensitive adhesives, agrochemicals, pharmaceuticals and other fine chemicals. Naphtha cracking is, however, in decline with the increase in availability of inexpensive natural gas supplies, and recovery from a byproduct stream in ethylene manufacture involves an extraction step conducted under tightly controlled conditions—so that derivation is from increasingly scarce and costly crude oil sources by a series of extraction steps.

The capability of thus making both renewable isobutene and renewable isoprene using a mixed acetic acid/propionic acid feed, whether generated by fermentation of sugars from biomass or from ethylene glycol and propylene glycol from the hydrogenolysis of one or more of glycerol, the five and six carbon sugars and sugar alcohols, lactate and lactic acid, consequently helps meet a continuing need of renewable and more sustainable alternatives to fossil fuel-based, nonrenewable commercial products.

BRIEF DESCRIPTION OF THE DRAWING

FIG. 1 schematically depicts a process of converting a combination of acetic acid and propionic acid to isobutene and isoprene in the presence of a catalyst, according to the first aspect.

DETAILED DESCRIPTION OF PREFERRED EMBODIMENTS

Referring now to FIG. 1, a process 10 is schematically illustrated wherein a mixed acid feedstock 12 comprising both acetic acid and propionic acid, but preferably having acetic acid and propionic acid as the two most prevalent acids therein, is converted in the presence of a catalyst, particularly, a $Zn_xZr_yO_z$ mixed oxide catalyst, to a isobutene and isoprene precursor-containing product 14 inclusive of both isobutene and certain $C_5$ intermediate products that may be converted to isoprene, for example, 2-methyl-1-butene and 2-methyl-2-butene (also known as isoamylene), the product 14 is resolved into an isobutene product 16 and a $C_5$ intermediates remainder 18 (which intermediates are hereinafter referred to for convenience as "$C_5$ isoprene precursors").

In a first embodiment, a $Zn_xZr_yO_z$ mixed oxide catalyst useful for the conversion of the acetic acid and propionic acid in the mixed acid feedstock 12 as described can be made by a "hard template" or "confined space synthesis" method generally of the character used by Jacobsen et al., "Mesoporous Zeolite Single Crystals", Journal of the American Chemical Society, vol. 122, pp. 7116-7117 (2000), wherein nanozeolites were prepared.

More particularly, the same carbon black (BP 2000, Cabot Corp.) may be used as a hard template for the synthesis of nanosized $Zn_xZr_yO_z$ mixed oxides, rather than nanozeolites as in Jacobsen et al. Prior to use, the BP 2000 template is dried, for example, at 180° C. overnight. Calculated amounts of zirconyl nitrate hydrate (Sigma-Aldrich, greater than 99.8% purity) and $Zn(NO_3)_2.6H_2O$ (Sigma-Aldrich, greater than 99.8% purity) are dissolved in a given amount of water, and sonicated for 15 minutes to produce a clear solution with desired concentrations of Zn and Zr. In one preparation, about 25 grams of the obtained solution are then mixed with 6.0 grams of the preheated BP 2000 to achieve incipient wetness, and the mixture is transferred to a ceramic crucible and calcined at 400 degrees Celsius for 4 hours, followed by ramping the temperature to 550 degrees Celsius (at a ramp rate of 3 degrees Celsius/minute) and holding at 550 degrees Celsius for another 20 hours. Nanosized white powders are obtained, having a mean particle size of less than 10 nanometers.

The nanosized $Zn_xZr_yO_z$ mixed oxide catalysts made by a hard template method are further described in Sun et al., "Direct Conversion of Bio-ethanol to Isobutene on Nanosized $Zn_xZr_yO_z$ Mixed Oxides with Balanced Acid-Base Sites", Journal of the American Chemical Society, vol. 133, pp. 11096-11099 (2011), along with findings related to the character of the mixed oxide catalysts formed thereby and the performance of the catalysts for the ethanol to isobutene conversion, given certain Zn/Zr ratios, residence times and reaction temperatures.

Alternatively, the $Zn_xZr_yO_z$ mixed oxide catalysts may be made as described in copending U.S. Patent Application Ser. No. 61/720,433, filed Oct. 31, 2012 for "Stable Mixed Oxide Catalysts for Direct Conversion of Ethanol to Isobutene and Process for Making" (the '433 application), by a process broadly comprising, in certain embodiments, forming a solution of one or more Zn compounds, combining one or more zirconium-containing solids with the solution of one or more Zn compounds so that the solution wets the zirconium-containing solids to a state of incipient wetness, drying the wetted solids, then calcining the dried solids. In other embodiments, a solution is formed of one or more Zr compounds, the solution is combined with one or more Zn-containing solids so that the solution wets the Zn-containing solids to a state of incipient wetness, the wetted solids are dried and then the dried solids are calcined.

In certain embodiments, the $Zn_xZr_yO_z$ mixed oxide catalysts (whether made by the hard template or incipient wetness methods) are characterized by a Zn/Zr ratio (x:y) of from about 1:100 to about 10:1, preferably from about 1:30 to about 1:1, especially about 1:20 to about 1:5, and still more preferably about 1:12 to about 1:10.

The catalysts made by the alternative, incipient wetness method are consistent in their particle size with the catalysts described in the incorporated journal article, namely, comprising aggregates of less than 10 nm-sized particles with a highly crystalline structure. The Zn oxide component is again highly dispersed on the Zr oxide component.

In certain embodiments, the $Zn_xZr_yO_z$ mixed oxide catalysts are characterized as low sulfur catalysts, containing less than about 0.14 percent by weight of sulfur. In the '433 application, it was reported in this regard that catalysts made by the incipient wetness method would desirably be substantially sulfur-free, preferably including less than about 0.01 percent by weight of sulfur and more preferably including less than about 0.001 weight percent of sulfur. In the '433 application, it was postulated that the reduced sulfur content enabled by the incipient wetness method as compared to the hard template method contributed significantly to the much improved stability observed for the incipient wetness method catalysts of the prior related application for the ethanol to isobutene process.

In converting acetic acid to isobutene, however, in at least some embodiments and under certain process conditions some sulfur does appear to be beneficial, though as just indicated, it is expected that the amount of sulfur will preferably be such that the catalysts are characterized as low sulfur catalysts. Such low sulfur catalysts are most readily made by the incipient wetness method described briefly above and in greater detail in the '433 application.

In principle, provided the zinc and zirconium compounds and solids in these embodiments have a sufficiently low sulfur content in order to produce a low sulfur content when combined according to the incipient wetness method, any combination of zinc and zirconium materials and any solvent can be used that will permit the zinc and zirconium components to mix homogeneously whereby, through incipient wetness impregnation, one of the zinc or zirconium components are well dispersed on a solid of the other component for subsequent drying and conversion to the oxide forms through calcining. Low sulfur catalysts can also be made by the incipient wetness method starting with zinc and zirconium compounds that are sulfur-free or substantially sulfur-free, then doping in a desired sulfur content into the $Zn_xZr_yO_z$ mixed oxide catalysts.

The conditions and times for the drying and calcining steps of an incipient wetness preparation will depend, of course, on the particular zinc and zirconium materials and solvent used, but in general terms, the drying step can be accomplished in a temperature range of from about 60 degrees Celsius to about 200 degrees Celsius over at least about 3 hours, while the calcining can take place at a temperature of from about 300 degrees Celsius to about 1500 degrees Celsius, but more preferably a temperature of from about 400 to 600 degrees Celsius is used. The calcination time can be from about 10 minutes to about 48 hours, with from about 2 to about 10 hours being preferred.

In still other embodiments, low sulfur catalysts could be prepared by a hard template method, except that a suitably very low sulfur content carbon is used for the hard template to realize a low sulfur content in the finished catalyst.

In certain embodiments, the conversion of the acetic acid and propionic acid in mixed acid feed 12 to isobutene and to the $C_5$ isoprene precursors, respectively, in the product 14 can be accomplished continuously in the gas phase, using a fixed bed reactor or flow bed reactor. The reaction temperature may be in a range from about 350 to about 700 degrees Celsius, preferably, in a range from about 400 to about 500 degrees Celsius, and the WHSV can be in a range from about 0.01 $hr^{-1}$ to about 10 $hr^{-1}$, preferably from about 0.05 $hr^{-1}$ to about 2 $hr^{-1}$. Acetic/propionic acid/water solutions with steam to carbon ratios from 0 to 20, preferably from 2 to 5 can be used to provide the acetic and propionic acids to the catalyst. An inert carrier gas, such as nitrogen, carbon dioxide or air, can be used.

As previously mentioned, the mixed acid feedstock 12 comprising both acetic and propionic acids (preferably as the two most prevalent acids) can be realized in a number of ways. For example, the feed 12 can be, or can be obtained from, a fermentation broth containing both acetic and propionic acids from the fermentation of sugars from lignocellulosic biomass.

Those skilled in the art will be familiar with various fermentations of this character, as well as other fermentations that will provide a mixed acid broth comprising acetic and/or propionic acids as targeted products. Examples of the latter may be found in the literature related to various methods that have been proposed and evaluated for the production of propionic acid by fermentation.

In this regard, while commercial production of propionic acid to date has been entirely by petrochemical routes, a variety of proposed fermentation methods have been evaluated for the industrial production of propionic acid from as early as about 1920, see Playne, "Propionic and Butyric Acids", Comprehensive Biotechnology: The Principles, Applications and Regulations of Biotechnology in Industry, Agriculture and Medicine, Volume 3, Pergamon Press, New York, N.Y. (1985) at pages 731-759, now incorporated by reference herein. One reason given by Playne for the absence of a commercial fermentation route to propionic acid is that acetic acid has been produced as a significant co-product, which in the context of the present invention obviously represents an advantageous feature. Bacteria listed by Playne as of "major importance" for the production of propionic acid from sugars, lactose or lactate through a dicarboxylic acid or acrylic acid metabolic pathway include *Propioibacterium*, especially *P. shermanii; Veillonella parvula; Veillonella alcalescens; Selenomonas ruminantium* (ph 5); *Selenomonas sputigena* (pH 5); *Clostridium propionicum; Clostridium novyi; Megasphaera elsdenii* (pH 4-8); *Bacteroides fragilis; Bacteroides ruminicola*; and *Fusobacterium necrophorum*.

Efforts to produce propionic acid by fermentation methods have continued in recent years, with various approaches being described for producing propionic acid as well as some acetic acid in greater and lesser proportions from glucose, lactose, sucrose, xylose, fructose, maltose and lactate substrates. References describing these efforts include WO 2012/064883 to Yang et. al. (describing metabolically engineered organisms for producing propionic acid with increased yield and productivity, and increased tolerance to propionic acid and acidic pHs); Lewis and Yang, "Propionic acid fermentation by *Propionibaterium acidipropionici*: effect of growth substrate", Appl. Microbiol. Biotechnol., 37:437-442 (1992); Wang and Yang, "Propionic acid production in glycerol/glucose co-fermentation by *Propionibacterium freudenreichii* subsp. *Shermanii*", Bioresour. Technol., 137:116-123 (June 2013); and Zhang and Yang, "Engineering *Propionibacterium acidipropionici* for enhanced propionic acid tolerance and fermentation", Biotechnol. Bioeng., vol. 104, no. 4, pp. 766-773 (Nov. 1, 2009). Additional reduced biobased substrates, for example, glycerol, are taught as useful in some fermentations for improving the redox balance and the yield and selectivity to propionic acid.

While a single fermentation may thus be employed to provide a mixed acid feedstock 12, both because of the well-appreciated difficulties associated with mixed acid fermentations generally and because of the improved flexibility afforded to provide mixed acid feedstocks 12 of differing compositions, it is expected that preferably separate fermentations will be employed to preferentially generate propionic acid on the one hand (building upon some of the above-referenced recent advancements in propionic acid fermentations, for example) and acetic acid on the other. The propionic acid and acetic acid can then be conventionally recovered from the individual fermentation broths and recombined to provide a mixed acid feedstock 12, or acetic acid or propionic acid can be recovered from its respective fermentation broth for combining into the other fermentation broth to yield the mixed acid feedstock 12, or the individual broths from the two fermentations can be combined to provide the mixed acid feedstock 12.

The production of acetic acid by fermentation fits very well with an independent fermentation mode of generating the mixed acid feedstock 12, in that various homoacetogenic microorganisms are known which are able through fermentation to produce acetic acid with 100% carbon yield; these microorganisms internally convert carbon dioxide to acetate, in contrast to a process for producing ethanol from sugars obtained from biomass, wherein carbon dioxide is produced as a byproduct.

Examples of homoacetogens given by U.S. Pat. No. 8,252, 567 are microorganisms of the genus *Moorella* and *Clostridium*, especially microorganisms of the species *Moorella thermoaceticum* (described as formerly classified as *Clostridium thermoaceticum*) or *Clostridium formicoaceticum*. U.S. Pat. No. 8,252,567 represents that about one hundred known acetogens in twenty-two genera were known as of 2009, and cross-references Drake, et al., Ann. NY Acad. Sci. 1125: 100-128 (2008) for a review of acetogenic microorganisms.

Other references describing fermentation methods for producing acetic acid from five and six carbon sugars include U.S. Pat. No. 4,935,360; U.S. Pat. No. 8,236,534; U.S. Pat. No. 4,513,084; U.S. Pat. No. 4,371,619 and U.S. Pat. No. 4,506,012; both one-step fermentation processes from the sugars to acetic acid, acetates or both are disclosed, as well as two-step processes involving a first fermentation to lactic acid (by *lactobacillus* or known methods of homolactic fermentation, preferably) followed by a second fermentation to convert lactic acid to acetic acid, for example, using *Clostridium formicoaceticum*.

Any of the known fermentation methods may, in short, be used to produce acetic acid for combining with propionic acid in the mixed acid feedstock 12, but homoacetogenic fermentation methods are considered preferable at least in that carbon dioxide is not produced as a byproduct—the carbon dioxide represents a yield loss from the overall process to make isobutene and as a greenhouse gas is undesirable particularly in the context of a process to make a needed product more sustainably from renewable resources.

The mixed acid feedstock 12 can in another embodiment be provided in whole or in part from a process for producing 1,2-propanediol (propylene glycol) by the hydrogenolysis of a feedstock selected from one or more of glycerol, the five and six carbon sugars and sugar alcohols, lactate and lactic acid in the presence of hydrogen and a suitable hydrogenolysis catalyst and under conditions which are effective for carrying out the hydrogenolysis. Ethylene glycol produced in such a process can be dehydrated and then the product of that dehydration step can be oxidized to provide acetic acid for the mixed acid feedstock 12, while at least a portion of the propylene glycol from the hydrogenolysis process can be dehydrated, and the product of the dehydration step then likewise oxidized to propionic acid for the mixed acid feed 12.

Propylene glycol and ethylene glycol have conventionally been produced from petrochemical sources. However, in recent years much research has taken place to develop suitable biobased propylene glycol and ethylene glycol products, which can be interchangeable with propylene glycol and ethylene glycol products deriving from petroleum refining and processing methods but which are made from renewable versus nonrenewable materials.

As a result of these efforts, processes have been developed by several parties involving the hydrogenolysis of especially five and six carbon sugars and/or sugar alcohols, whereby the higher carbohydrates are broken into fragments of lower molecular weight to form compounds which belong to the glycol or polyol family. Sugars containing five carbon chains, such as ribose, arabinose, xylose and lyxose, and corresponding five carbon chain sugar alcohols such as xylitol and arabinitol, are among the materials contemplated in U.S. Pat. No. 7,038,094 to Werpy et al., for example, as are lactic acid, lactate and six carbon sugars such as glucose, galactose, maltose, lactose, sucrose, allose, altrose, mannose, gulose, idose and talose and six carbon chain sugar alcohols such as sorbitol. Some of these carbohydrate-based feedstocks are commercially available as pure or purified materials. These materials may also be obtained as side-products or even waste products from other processes, such as corn processing. The sugar alcohols may also be intermediate products produced in the initial stage of hydrogenating a sugar.

For other known examples of such processes, U.S. Pat. No. 5,206,927 describes a homogeneous process for hydrocracking carbohydrates in the presence of a soluble transition metal catalyst to produce lower polyhydric alcohols. A carbohydrate is contacted with hydrogen in the presence of a soluble transition metal catalyst and a strong base at a temperature of from about 25° C. to about 200° C. and a pressure of from about 15 to about 3000 psi. However, as is evident from Tables II and III in the disclosure of U.S. Pat. No. 5,206,927, about 2-7% of other polyol compounds are produced in the hydrocracking process. U.S. Pat. No. 4,476,331 describes a two stage method of hydrocracking carbohydrates using a modified ruthenium catalyst. European Patent Applications EP-A-0523 014 and EP-A-0 415 202 describe a process for preparing lower polyhydric alcohols by catalytic hydrocracking of aqueous sucrose solutions at elevated temperature and pressure using a catalyst whose active material comprises the metals cobalt, copper and manganese. Still other examples of such carbohydrate-based processes may be found without difficulty by those skilled in the art.

Other efforts have been based on the use of another readily accessible biobased feedstock, namely, glycerol. Glycerol is currently produced as a byproduct in making biodiesel from vegetable and plant oils, through the transesterification reaction of lower alkanols with higher fatty acid triglycerides to yield lower alkyl esters of higher fatty acids and a substantial glycerol byproduct. Glycerol is also available as a by-product of the hydrolysis reaction of water with higher fatty acid triglycerides to yield soap and glycerol. The higher fatty acid triglycerides may derive from animal or vegetable (plant) sources, or from a combination of animal and vegetable sources as well known, and a variety of processes have been described or are known.

A biobased glycerol is also available as a product of the hydrogenolysis of sorbitol, as described in an exemplary process in U.S. Pat. No. 4,366,332, issued Dec. 28, 1982.

U.S. Pat. Nos. 5,276,181 and 5,214,219 thus describe a process of hydrogenolysis of glycerol using copper and zinc catalyst in addition to sulfided ruthenium catalyst at a pressure over 2100 psi and temperature between 240-270° C.

U.S. Pat. No. 5,616,817 describes a process of preparing 1,2-propanediol (more commonly, propylene glycol) by catalytic hydrogenolysis of glycerol at elevated temperature and pressure using a catalyst comprising the metals cobalt, copper, manganese and molybdenum.

German Patent DE 541362 describes the hydrogenolysis of glycerol with a nickel catalyst.

Persoa & Tundo (Ind. Eng. Chem. Res. (2005), pp 8535-8537) describe a process for converting glycerol to 1,2-propanediol by heating under low hydrogen pressure in presence of Raney nickel and a liquid phosphonium salt. Selectivities toward 1,2-propanediol as high as 93% were reported, but required using a pure glycerol and long reaction times (20 hrs).

Crabtree et al. (Hydrocarbon Processing, February 2006, pp 87-92) describe a phosphine/precious metal salt catalyst that permit a homogenous catalyst system for converting glycerol into 1,2-propanediol. However, low selectivity (20-30%) was reported.

Other reports indicate use of Raney copper (Montassier et al., Bull. Soc. Chim. Fr., vol. 2, pg 148 (1989); Stud. Surf. Sci. Catal., vol. 41, p. 165 (1988)), copper on carbon (Montassier et al., J. Appl. Catal. A, vol. 121, p. 231 (1995)), copper-platinum and copper ruthenium (Montassier et al., J. Mol. Catal., vol. 70, p. 65 (1991)).

Still other homogenous catalyst systems such as tungsten and Group VIII metal-containing catalyst compositions have been also tried (U.S. Pat. No. 4,642,394). Miyazawa et al. (J. Catal., vol. 240, pp. 213-221 (2006)) & Kusunoki et al (Catal. Comm., vol. 6, pp. 645-649 (2005)) describe a Ru/C and ion exchange resin for conversion of glycerol in aqueous solution. Again their process however, results in low conversions of glycerol (0.9-12.9%).

One of the recognized problems in producing a biobased propylene glycol or ethylene glycol by such methods, is that other diol compounds are formed which reduce the purity of the desired component. The boiling points of many of these are very close to one another, however, so that the separation of substantially pure propylene glycol from these other polyhydric alcohols is difficult. Various processes have accordingly been proposed for accomplishing the refining of the hydrogenolysis products. WO 2012/125276 to Adlaf et al. discusses several of the approaches taken by the hydrogenolysis art, and describes distillation schemes whereby mixed ethylene glycol and propylene glycol streams are generated which could be used to provide a mixed acid feedstock 12 including acetic and propionic acids. Those skilled in the art will, of course, appreciate that each of the many published hydrogenolysis methods may be considered for providing the ethylene glycol and propylene glycol from among the unrefined or refined streams found in a given method, whether from a single mixed stream containing both or from a plurality of sources.

The ethylene glycol and propylene glycol in any event may be converted to acetic acid and propionic acid, respectively, for the mixed acid feedstock 12 by first dehydrating the ethylene glycol and propylene glycol to their corresponding aldehydes acetaldehyde and propionaldehyde, then oxidizing the acetaldehyde and propionaldehyde to provide acetic acid and propionic acid. Various catalysts for the dehydration of propylene glycol (1,2-propanediol) have been evaluated and are available from the prior art, see, for example, Mori et al., "Catalytic dehydration of 1,2-propanediol into propanal", Applied Catalysis A: General, vol. 366, pp. 304-308 (2009) (finding acidic inorganic oxides and supported heteropolyacids useful for a vapor phase dehydration, especially, silica-supported heteropolyacids with an aqueous propylene glycol feed); Sugiyama et al., "The Catalytic Conversion of 1,2-Propanediol to Propanal on FSM-16 Molded by Wet-Treatment and Pressurization", Journal of Chemical Engineering of Japan, vol. 46, no. 9, pp 620-624 (2013)(FSM-16 being described as a mesoporous silica); Cherysheva et al., "Nature of the Products from the Catalytic Dehydration of Propylene Glycol", Zhurnal Organicheskoi Khimii, vol. 7, no. 1, p. 212 (January 1971)(cation-exchange resins, p-toluenesulfonic acid and sulfuric acid); and Zhang et al., "Dehydration of 1,2-propanediol to propionaldehyde over zeolite catalysts", Applied Catalysis A: General, vol. 400, pp 148-155 (2011) (discussing prior studies with electrophilic, nucleophilic and lanthanide oxide catalysts in evaluating (and finding effective) zeolites such as ZSM-5). A number of examples of the dehydration of ethylene glycol to acetaldehyde are similarly available in the prior art, as referenced and summarized by Smith, "Ethylene glycol to acetaldehyde—dehydration or a concerted mechanism", Tetrahedron, vol. 58, pp. 2091-2094 (2002). Parenthetically, it is contemplated that the dehydrations of propylene glycol and of ethylene glycol can be done on a mixture of the glycols, or on the propylene glycol and ethylene glycol separately and independently.

The subsequent oxidation of the acetaldehyde and propionaldehyde dehydration products to provide acetic and propionic acids can be done by any conventionally known oxidation method. In this regard, as described in Sano et al., "Acetic acid production by direct oxidation of ethylene", Chem. Eng. Technol., vol. 29, no. 11, pp. 1376-1380 (2006), the primary method for producing acetic acid commercially for many years was by oxidation of acetaldehyde in the presence of a manganese acetate catalyst, though this method has now been supplanted by carbonylation of methanol. Catalytic methods for the oxidation of propionaldehyde to yield propionic acid have likewise been described, which have principally involved vanadium oxide and vanadium phosphate catalysts, see Slavucha et al., Catal. Lett., No. 2, page 257 (1989) and Ai et al., Bull. Chem. Soc. Jpn., no. 67, pg. 551 (1994); the oxidation of a mixture of acetaldehyde and propionaldehyde has likewise been described on a titania-supported vanadium oxide catalyst in the presence of water vapor, see Suprun et al., Chem. Eng. Technol., vol. 29, no. 11, pp 1376-1380 (2006). Consequently, it is contemplated that the oxidation step can likewise be conducted on a mixture of the acetaldehyde and propionaldehyde dehydration products or on the acetaldehyde and propionaldehyde individually, but those skilled in the art will be well able in any event to determine how best to conduct the dehydration and oxidation steps on the ethylene glycol and propylene glycol from a preceding hydrogenolysis process in order to provide the acetic and propionic acids for mixed acid feedstock 12.

The mixed acid feedstock 12 is then in preferred embodiments converted as described previously to an isobutene and isoprene precursor-containing product 14 inclusive of both isobutene and certain $C_5$ intermediate products that may be converted to isoprene, for example, 2-methyl-1-butene and 2-methyl-2-butene (also known as isoamylene), in the presence of a $Zn_xZr_yO_z$ mixed oxide catalyst. The product 14 will also contain acetone, methyl ethyl ketone and sundry gases. The acetone and methyl ethyl ketone are readily separated from the isobutene and the $C_5$ isoprene precursors on the basis of differences in the volatilities of these materials, and then isobutene 16 is separated out from a $C_5$ intermediates remainder 18 by distillation. The $C_5$ isoprene precursors in remainder 18 are then dehydrogenated to isoprene 20, by any one of a variety of known methods.

In this regard, as related in US 2010/0022816 to Merrill, for example (such publication now being incorporated herein by reference), the two $C_5$ isoprene precursors that result from (it is believed) a condensation of an acetone intermediate from the acetic acid in the mixed acid feedstock 12 and the methyl ethyl ketone intermediate from the propionic acid in the feedstock 12—namely, 2-methyl-1-butene and 2-methyl-2-butene—may be found in current $C_5$ refinery streams from petroleum refining; these isoamylene monomers are presently catalytically dehydrogenated by refinery operators in the presence of oxygen to provide isoprene. The oxygen is typically provided in the form of steam. US 2010/022816 to Merrill seeks to use equipment and catalysts typically used for dehydrogenating ethylbenzene to styrene (such as a ferric oxide, potassium carbonate-based dehydrogenation catalyst as sold by Sud-Chemie under the tradename "Styromax Plus" or as sold by Criterion as "Hypercat GV"), with increased catalyst life but while avoiding the steam regeneration cycles which had previously been necessary. Those skilled in the art will appreciate that still other catalysts are known and could be used as desired to carry out the dehydrogenation step to isoprene 20, for example, simple iron oxide catalysts (RU 213774C1 to Kovalenko et al.), nickel-alumina and nickel-calcium phosphate catalysts doped or not with zinc or strontium, aluminum-molybdenum-chromium oxide catalysts, bismuth molybdate catalysts, and mixed oxide catalysts as described in JP 55084541.

The present methods will be further illustrated by the following non-limiting examples:

EXAMPLES

Example 1

Commercial zirconium hydroxide was dried at 120 degrees Celsius for more than 5 hours. A calculated amount of $Zn(NO_3)_2$ (from Sigma-Aldrich, more than 99.8 percent purity) was dissolved in water, forming a clear solution. The dried zirconium hydroxide (which was also from Sigma-Aldrich, more than 99.8 percent purity) was then mixed with the solution by incipient wetness, in order to form wet powders impregnated with Zn. The wetted powder was then dried at 80 degrees Celsius for 4 hours, followed by calcination at 550 degrees Celsius for 3 hours, to obtain a $Zn_1Zr_8O_z$ catalyst by the incipient wetness impregnation method of the '312 application.

An acetic acid to isobutene process was conducted (as described in the '433 application) with the catalyst thus prepared in a fixed-bed stainless steel reactor having an inside diameter of 5 millimeters. 100 mg of the catalyst was packed between quartz wool beds. A thermocouple was placed in the middle of the catalyst bed to monitor the reaction temperature. Before beginning the reaction, the catalyst bed was pretreated by flowing 50 ml/minute of nitrogen at 450 degrees Celsius through the catalyst over a half hour. A 25 weight percent solution of acetic acid in water was then introduced into an evaporator at 180 degrees Celsius by means of a syringe pump, and the vaporized steam/acetic acid was carried into the reactor by a flowing nitrogen carrier gas at an acetic acid concentration in the gas phase of 1.36 weight percent and a WHSV of 0.1 grams of acetic acid per gram of catalyst per hour. Meanwhile, the product line was heated to in excess of 150 degrees Celsius before a cold trap, to avoid condensing the liquid products in the product line. A reaction temperature of 415 degrees Celsius was employed.

A Shimadzu 2400 gas chromatograph equipped with an auto sampling valve, HP-Plot Q column (30 m, 0.53 mm, 40 μm) and flame ionization detector was connected to the line between the reactor outlet and cold trap to collect and analyze the products in the effluent gas. After the cold trap, an online micro-GC (MicroGC 3000A equipped with molecular sieves 5A, plot U columns and thermal conductivity detectors) was used to analyze the product gases specifically, using nitrogen as a reference gas.

A consistent product of about 5 percent by weight of methane, about 10 percent by weight of acetone, about 33 percent by weight of carbon dioxide and more than about 50 percent by weight of the desired isobutene product was obtained; in contrast to an ethanol to isobutene process using these same $Zn_xZr_yO_z$ mixed oxide catalysts, no ethylene or propylene was produced. The catalyst showed very high stability over the full duration of the run, with no signs of observable deactivation after more than 1400 minutes of time-on-stream operation.

Examples 2 through 10

For these additional examples of converting acetic acid to isobutene, additional $Zn_xZr_yO_z$ mixed oxide catalysts were prepared both by the incipient wetness method (IW in the tabulated results below) but also by the prior art hard template method (HT) described in the Sun et al. journal article (2011), and these were evaluated and the products analyzed using the same apparatus and method described above but under different sets of reaction conditions (as summarized in Table 1 below).

TABLE 1

Additional Acetic Acid Examples

| Ex # | Catalyst | Zn/Zr ratio | Reaction temp. (° C.) | WHSV ($g_{acetic}/g_{catal}$/hr) | Steam to carbon ratio | $C_{G\text{-}acetic\ acid}$ (wt %) | Acetone selectivity (mol %) | Isobutene selectivity (mol %) |
|---|---|---|---|---|---|---|---|---|
| 2 | HT | 1/15 | 450 | 0.25 | 5 | 1.3 | 30.5 | 41.7 |
| 3 | HT | 1/15 | 450 | 1.14 | 5 | 1.5 | 61.1 | 18.4 |
| 4 | IW | 1/8 | 415 | 0.1 | 5 | 1.4 | 9.8 | 52.5 |
| 5 | IW | 1/10 | 415 | 0.95 | 5 | 22.3 | 50.8 | 20.1 |
| 6 | IW | 1/10 | 450 | 0.16 | 2.5 | 18.8 | 0.7 | 50.6 |
| 7 | IW | 1/10 | 450 | 0.65 | 2.5 | 18.8 | 8.3 | 46.9 |
| 8 | IW | 1/10 | 415 | 0.16 | 2.5 | 18.8 | 5.7 | 57.2 |
| 9 | IW | 1/10 | 415 | 0.33 | 2.5 | 18.8 | 16.4 | 45.3 |
| 10 | IW | 1/10 | 415 | 0.65 | 2.5 | 18.8 | 30.5 | 35.0 |

Example 11

For this example, a mixed acids feed generated by the oxidation of a mixed propylene glycol/ethylene glycol byproduct stream from the hydrogenolysis of glycerol according to WO 2012/125276 to Adlaf et al. was supplied to a $Zn_1Zr_{10}O_z$ catalyst prepared by the incipient wetness method of the '433 application, in the apparatus and according to the procedure of Examples 1-10. At a reaction temperature of 415 degrees Celsius, and at a WHSV of 0.1 hr$^{-1}$ and a steam to carbon ratio of 5:1 as in Example 1, isobutene was produced at a selectivity of 49.5 mol percent while 2-methyl-2-butene and 2-methyl-1-butene were produced at about 2 mol percent from propionic acid in the oxidized hydrogenolysis byproduct stream.

Example 12

A first, dehydration reactor was set up to carry out a vapor phase dehydration of 1.5 ml/minute of a 30 weight percent solution of ethylene glycol in water, using a jacket temperature of 300 degrees Celsius, a nitrogen carrier gas at 700 ml/minute and using 30 cubic centimeters of a commercially available, 18% tungstated zirconia catalyst. The dehydration reactor products were then supplied without any intermediate purification or isolation step to a second, oxidation reactor maintained at the same jacket temperature, with 850 ml/minute of air over 150 cubic centimeters of a commercially available acrylic acid catalyst. Three random samples of the product mixture from the oxidation reactor showed acetic acid to be the major product, at 15.286%, 19.862% and 21.06% (by weight) for the three samples.

Example 13

A second run was conducted as described in Example 12, except that a single composite sample was taken over the course of the seven hour experiment. This composite sample was comprised of 19.723 percent acetic acid by weight, representing a weight yield of 65.9 percent as acetic acid from the ethylene glycol supplied to the dehydration and oxidation reactors in series.

Example 14

A first, dehydration reactor was set up to carry out a vapor phase dehydration of 1.5 ml/minute of a 60 weight percent solution of propylene glycol in water, using a jacket temperature of 300 degrees Celsius, a nitrogen carrier gas at 700 ml/minute and using 30 cubic centimeters of a commercially available, 18% tungstated zirconia catalyst. The dehydration reactor products were then supplied without any intermediate purification or isolation step to a second, oxidation reactor maintained at the same jacket temperature, with 750 ml/minute of air over 150 cubic centimeters of a commercially available acrylic acid catalyst. Two random samples of the product mixture from the oxidation reactor showed propionic acid to be the major product, at 13.938%, 18.542% (by weight) for the two samples.

Example 15

A second run was conducted as described in Example 14, except that the feed concentration was 30% (w/w) of propylene glycol and the dehydration reactor was maintained at 225° C. A single composite sample was taken over the course of the seven hour experiment. This composite sample was comprised of 19.1 percent propionic acid by weight, representing a weight yield of 63.43 percent as propionic acid from the propylene glycol supplied to the dehydration and oxidation reactors in series.

Examples 16-23

For these examples, various mixed propionic acid/acetic acid feeds were supplied to a $Zn_1Zr_{10}O_z$ catalyst prepared by the incipient wetness method of the '433 application, in the apparatus and according to the procedure of Examples 1-10. At a reaction temperature of 415 degrees Celsius and a steam to carbon ratio again of 5:1, with other conditions (WHSV, for example) being as indicated in Table 2 immediately following, these mixtures of propionic and acetic acids in various proportions produced different amounts of isobutene and other products of interest. "MEK" in the table refers to methyl ethyl ketone, whereas "C5" refers to 2-methyl-1-butene and 2-methyl-2-butene, and "C6" refers to two evident C6 products, presently believed to be 3-methyl-2-pentene and 2-ethyl-1-butene.

TABLE 2

Further mixed propionic acid and acetic acid examples

| Run # | Acetic acid to propionic acid ratio (Molar) | WHSV ($g_{acetic\ acid}/g_{catal}$/hr) | $C_{G\text{-}total\ acid}$ (wt %) | Acetone selectivity (mol %) | MEK$^Y$ selectivity (mol %) | 3-pentanone selectivity (mol %) | Isobutene selectivity (mol %) | C5 | C6 |
|---|---|---|---|---|---|---|---|---|---|
| 1 | 23.4 | 0.28 | 1.46 | 17.8 | 5.7 | 0.0 | 37.9 | 5.4 | 0.0 |
| 2 | 11.1 | 0.27 | 1.45 | 19.3 | 12.3 | 0.0 | 29.9 | 8.6 | 0.2 |
| 3 | 7.0 | 0.27 | 1.44 | 17.8 | 18.4 | 0.0 | 24.9 | 8.9 | 0.7 |
| 4 | 2.9 | 0.29 | 1.46 | 13.6 | 37.8 | 6.1 | 8.9 | 10.6 | 1.3 |
| 5 | 1.2 | 0.28 | 1.42 | 7.4 | 44.5 | 15.1 | 3.5 | 8.9 | 2.4 |
| 6 | 0.3 | 0.27 | 1.35 | 2.3 | 37.6 | 39.4 | 0.5 | 3.1 | 2.6 |
| 7 | 1.0 | 0.14 | 1.40 | 7.2 | 24.4 | 4.7 | 10.5 | 14.9 | 4.1 |
| 8 | 1.0 | 0.07 | 1.40 | 5.4 | 16.5 | 2.4 | 14.1 | 19.6 | 4.6 |

What is claimed is:

1. A process for making renewable isobutene and renewable isoprene, comprising:
   converting a mixed acid feed including acetic acid and propionic acid to a product mixture comprising isobutene and at least one or both of 2-methyl-1-butene and 2-methyl-2-butene, in the presence of a $Zn_xZr_yO_z$ mixed oxide catalyst having a ratio of x:y of from about 1:100 to about 10:1, at a temperature in the range of from about 350 to about 700 degrees and a WHSV in the range of from about 0.01 hr$^{-1}$ to about 10 hr$^{-1}$;
   separating isobutene from the product mixture; and
   dehydrogenating at least one or both of the 2-methyl-1-butene and 2-methyl-2-butene to produce isoprene.

2. A process according to claim 1, wherein the $Zn_xZr_yO_z$ mixed oxide catalyst contains less than about 0.14 percent by weight of sulfur.

3. A process according to claim 2, wherein the $Zn_xZr_yO_z$ mixed oxide catalyst contains less than about 0.01 percent by weight of sulfur.

4. A process according to claim 2, wherein the $Zn_xZr_yO_z$ mixed oxide catalyst contains less than about 0.001 percent by weight of sulfur.

5. A process according to claim 1, wherein x:y is from about 1:30 to about 1:1.

6. A process according to claim 5, wherein x:y is from about 1:20 to about 1:5.

7. A process according to claim 6, wherein x:y is from about 1:12 to about 1:10.

8. A process according to claim 1, wherein the mixed acid feed is or is obtained from a mixed acid fermentation broth from a fermentation of one or more of five carbon sugars, six carbon sugars, lactic acid and lactate substrates, wherein acetic acid and propionic acid are the two most prevalent acids.

9. A process according to claim 1, wherein the mixed acid feed is obtained by combining a fermentation broth from a fermentation preferentially producing acetic acid and a fermentation broth from a fermentation preferentially producing propionic acid.

10. A process according to either claim 8 or claim 9, wherein the mixed acid feed is supplied to the catalyst with steam in a steam to carbon ratio of from 0 to 20 wherein the carbon is determined on the basis of acetic acid and propionic acid content only.

11. A process according to claim 10, wherein the steam to carbon ratio is from 2 to 5.

12. A process according to claim 1, wherein the reaction temperature in the conversion of the mixed acid feed is from about 400 to about 500 degrees Celsius and the WHSV is from about 0.05 $hr^{-1}$ to about 2 $hr^{-1}$.

* * * * *